(12) United States Patent
Becker et al.

(10) Patent No.: US 8,354,836 B2
(45) Date of Patent: Jan. 15, 2013

(54) DEVICE AND PROCESS FOR DETECTING PARTICLES IN A FLOWING LIQUID

(75) Inventors: Edwin Becker, Reken (DE); Thomas Knoell, Neu-Ulm (DE); Roland Hoelzl, Munich (DE)

(73) Assignee: Prüftechnik Dieter Busch AG, Ismaning (DE)

( * ) Notice: Subject to any disclaimer, the term of this patent is extended or adjusted under 35 U.S.C. 154(b) by 690 days.

(21) Appl. No.: 11/958,001

(22) Filed: Dec. 17, 2007

(65) Prior Publication Data

US 2008/0150518 A1 Jun. 26, 2008

(30) Foreign Application Priority Data

Dec. 15, 2006 (DE) .......................... 10 2006 059 437
Aug. 21, 2007 (DE) .......................... 10 2007 039 435

(51) Int. Cl.
*G01N 27/72* (2006.01)
*G01R 33/12* (2006.01)

(52) U.S. Cl. ...................................... 324/204
(58) Field of Classification Search ............ 324/204
See application file for complete search history.

(56) References Cited

U.S. PATENT DOCUMENTS

| | | | | |
|---|---|---|---|---|
| 2,940,309 A * | 6/1960 | Karlby | ....................... | 73/861.351 |
| 3,017,256 A * | 1/1962 | Richardson | .................... | 422/111 |
| 3,249,861 A * | 5/1966 | Pevar | ............................ | 324/216 |
| 3,433,057 A * | 3/1969 | Halsey | .......................... | 73/61.71 |
| 3,575,050 A | 4/1971 | Lynnworth | | |
| 4,380,924 A | 4/1983 | Nakamoto et al. | | |
| 4,563,644 A * | 1/1986 | Lenander et al. | .............. | 324/232 |
| 4,613,815 A * | 9/1986 | Christel, Jr. | ..................... | 324/233 |
| 4,816,758 A * | 3/1989 | Theissen et al. | .............. | 324/204 |
| 4,837,511 A | 6/1989 | Whittington et al. | | |
| 4,926,120 A | 5/1990 | Veronesi et al. | | |
| 5,001,424 A * | 3/1991 | Kellett et al. | .................. | 324/204 |
| 5,315,243 A | 5/1994 | Kempster et al. | | |
| 5,444,367 A * | 8/1995 | Kempster et al. | .............. | 324/204 |
| 5,811,664 A | 9/1998 | Whittington et al. | | |
| 6,051,970 A * | 4/2000 | Hutchings | ...................... | 324/204 |
| 6,566,871 B2 | 5/2003 | Hölzl | | |
| 7,148,678 B1 * | 12/2006 | Targosz | .......................... | 324/204 |
| 7,443,156 B2 | 10/2008 | Hoelzl et al. | | |

(Continued)

FOREIGN PATENT DOCUMENTS

DE 2 108 717 9/1972

(Continued)

*Primary Examiner* — Jay Patidar
(74) *Attorney, Agent, or Firm* — Roberts Mlotkowski Safran & Cole, P.C.; David S. Safran

(57) ABSTRACT

A device for detecting electrically conductive particles in a liquid flowing in a pipe section, with a transmitter coil surrounding the pipe section for inducing eddy currents in the particles, at least one first inductive receiver coil surrounding the pipe section and a second inductive receiver coil which is spaced axially to the first receiver coil and which surrounds the pipe section, the first and the second receiver coils being located in the region of the transmitter coil and being subtractively connected, in order to output a difference signal according to the eddy currents induced by the transmitter coil, and the transmitter coil forming the primary side and the receiver coils forming the secondary side of a transformer arrangement. An evaluation unit evaluates the difference signal in order to detect passage of electrically conductive particles in the pipe section.

21 Claims, 3 Drawing Sheets

U.S. PATENT DOCUMENTS

| | | | |
|---|---|---|---|
| 7,737,683 B2 * | 6/2010 | Graze et al. | 324/204 |
| 2004/0169502 A1 * | 9/2004 | Julius | 324/204 |
| 2009/0189599 A1 * | 7/2009 | Fujii et al. | 324/204 |

FOREIGN PATENT DOCUMENTS

| | | |
|---|---|---|
| DE | 28 40 358 A1 | 3/1979 |
| DE | 28 50 246 A1 | 5/1980 |
| DE | 39 31 497 A1 | 4/1991 |
| DE | 40 14 756 A1 | 11/1991 |
| EP | 0 124 042 A2 | 11/1984 |
| EP | 0 451 209 B1 | 8/1994 |
| EP | 0 773 440 A1 | 5/1997 |
| GB | 2 165 650 A | 4/1986 |
| WO | 2004/081608 A2 | 9/2004 |
| WO | 2004/104561 A1 | 12/2004 |
| WO | 2006/007826 A1 | 1/2006 |
| WO | 2007/088015 A1 | 8/2007 |

* cited by examiner

DEVICE AND PROCESS FOR DETECTING PARTICLES IN A FLOWING LIQUID

BACKGROUND OF THE INVENTION

1. Field of Invention

The invention relates to a process and a device for detecting electrically conductive particles in a liquid flowing through a pipe by means of eddy currents.

2. Description of Related Art

German Patent Application DE 2 108 717 A1 describes a process and device of the type to which the present invention is directed in which two induction coils are located in two branches of an alternating current bridge circuit, the other two branches of which are formed by the halves of another coil. Liquid flows through the coils in the axial direction and the coils can be arranged in succession in the flow direction, the impedance changes which are caused by the passage of the particles and the difference of the impedance change in both coils being evaluated. An arrangement is shown in which the liquid flow is divided into two parallel component sections which each flow through one of the two coils, in which case an axial offset of the coils not necessary.

A similar device is described in German Patent Application DE 28 40 358 A1.

The company momac GmbH & Co. KG, 47408 Moers, Germany sells a device under the name "metalscan" in which three coils are arranged in succession in the flow direction, the first and the last coil acting as the transmitter coils and the middle coil acting as the receiver coil to detect passage of electrically conductive particles from a lubricant circuit. The first and the last coil are polarized in reverse.

Other devices in which the signal from the induction coils through which a liquid has flowed is used for particle detection are described for example, in International Patent Application Publications WO 2004/081608 and WO 2004/104561, European Patent Application EP 0 778 937 A2 (which corresponds to U.S. Pat. No. 5,811,664) and European Patent Application EP 0 451 209 B1.

German Patent Application DE 39 31 497 A1 discloses a process for inductive detection of particles in lubricants, a coupling coil embedded in a coil through which flow takes place axially being resonantly excited and the passage of particles being detected using the energy removed from the coil system by the eddy currents. In this connection, the particle size is determined from the signal amplitude. In order to prevent adulteration of the measurement by the coil sensitivity which decreases in the coil middle as compared to the coil edge, a swirl generator in the passage provides for the particles passing the coil to always be near the coil wall.

German Patent Application DE 31 17 319 A1 and corresponding U.S. Pat. No. 4,380,924 describe detection of the flow velocity of a liquid metal by means of eddy current measurement using a cross correlation function.

German Patent Application DE 40 14 756 A1 describes determination of the velocity of a body or material by means of eddy current measurement, a correlation function being formed.

U.S. Pat. No. 3,575,050 and German Patent Application DE 28 50 246 A1 mention that there are flowmeters based on eddy currents.

Furthermore, it is known that, in eddy current testing of metallic workpieces, a coil arrangement can be used in which there are subtractively connected receiver coils which are spaced apart in the lengthwise direction of the workpiece and which are surrounded externally by a transmitter coil which is located coaxially thereto. In eddy current testing, then, the workpiece is pushed through the interior of the two receiver coils. The transmitter coil forms the primary side and the receiver coils form the secondary side of a transformer arrangement. One example of this arrangement can be found in European Patent Application EP 1 189 058 A2 corresponding U.S. Pat. No. 6,566,871.

In eddy current testing of workpieces, the fact is used that defects in the material of the workpiece hinder the propagation of eddy currents which are induced by means of the transmitter coil; this acts on the electromagnetic field which has been produced by the eddy currents and which is detected in turn by a sensor which can be the transmitter coil itself or at least one separate receiver coil. If only a single separate receiver coil is provided, this arrangement is called an "absolute coil." Two or more measurement coils can be subtractively connected; this is then called a "difference coil" and enables, for example, temperature drift to be neutralized. If more than two receiver coils are used, this arrangement is also called a "multi-difference coil".

Similarly, electrically conductive particles in a liquid which is flowing through the coils cause eddy current losses which, in turn, are reflected in a measurable impedance change of the coils. In this way, by means of an inductive coil arrangement, electrically conductive particles in a liquid flowing in a tube can be detected. This is especially advantageous when the concentration of metallic particles in the lubricant circuit of a machine is to be detected in order to draw conclusions about the machine state (the concentration of metallic particles is generally a measurement for machine wear).

SUMMARY OF THE INVENTION

A primary object of this invention is to devise a process and apparatus for detecting electrically conductive particles in a liquid flowing through a pipe section with which accuracy as good as possible is to be achieved.

This object is achieved in accordance with the invention by a device by an advantageous approach in which the transmitter coil and the receiver coil form a transformer arrangement and the transmitter coil is located in the region of the receiver coils, so that all coils are located near one another, and thus, are exposed to essentially the same environmental influences, for example, with respect to temperature. As a result, measurement accuracy is increased.

The invention is explained in greater detailed below with reference to the accompanying drawings.

DETAILED DESCRIPTION OF THE INVENTION

Figure 1:
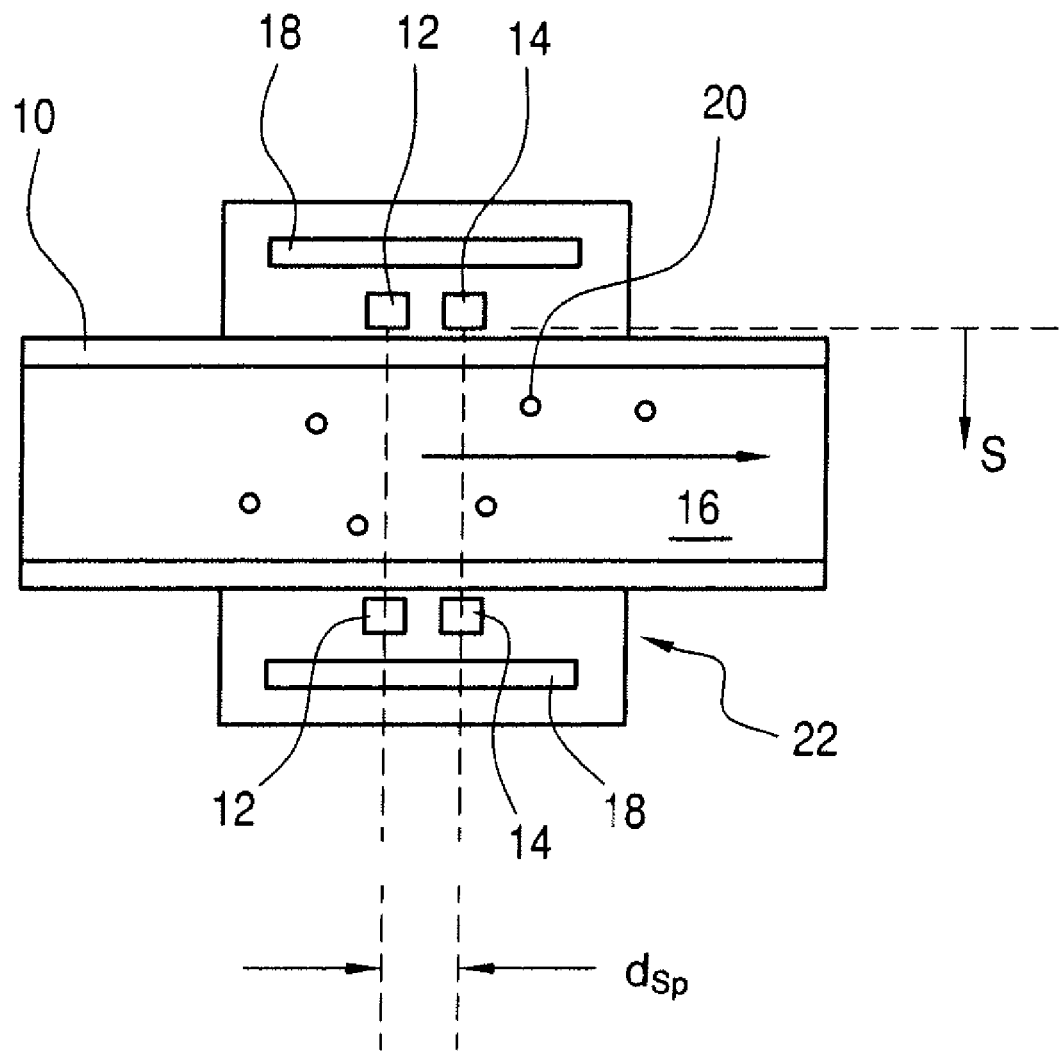
FIG. 1 schematically shows a lengthwise section through a pipe through which a liquid is flowing and which is provided with the coils of a device in accordance with the invention for detecting conductive particles in the liquid.

As shown in FIG. 1, a pipe section 10 is surrounded by a first inductive receiver coil 12 and a second inductive receiver coil 14 located spaced apart from it in the axial direction so that a liquid 16 which is flowing in the pipe section 10 flows through the coils 12 and 14 in the axial direction. The axial distance of the two coils 12, 14 and the axial dimension of the coils 12, 14 can be, for example, 2 mm. The two receiver coils 12, 14 are surrounded externally by a transmitter coil 18 which is located coaxially relative to the two coils 12, 14 and which has a greater diameter than the latter. The axial dimension of the transmitter coil 18 is such that the two receiver coils 12, 14 are located entirely within the transmitter coil 18. Preferably, the extension of the transmitter coil 18 in the axial direction is at least twice as great as the axial extension of the arrangement of the receiver coils 12, 14, i.e., distance plus axial extension of the coils 12, 14. The coils 12, 14, 18 are located in a housing 22 which surrounds the pipe section 10.

Typically, the pipe section 10 is part of the lubricant circuit of a machine, the liquid 16 then being a lubricant in which there are metallic particles which typically are the result of wear debris of moving parts of the machine. A typical value for the lubricant flow rate in the main flow is 10 liters/min. At much higher flow rates, it is a good idea to measure, not in the main flow, but a secondary flow.

Figure 2:
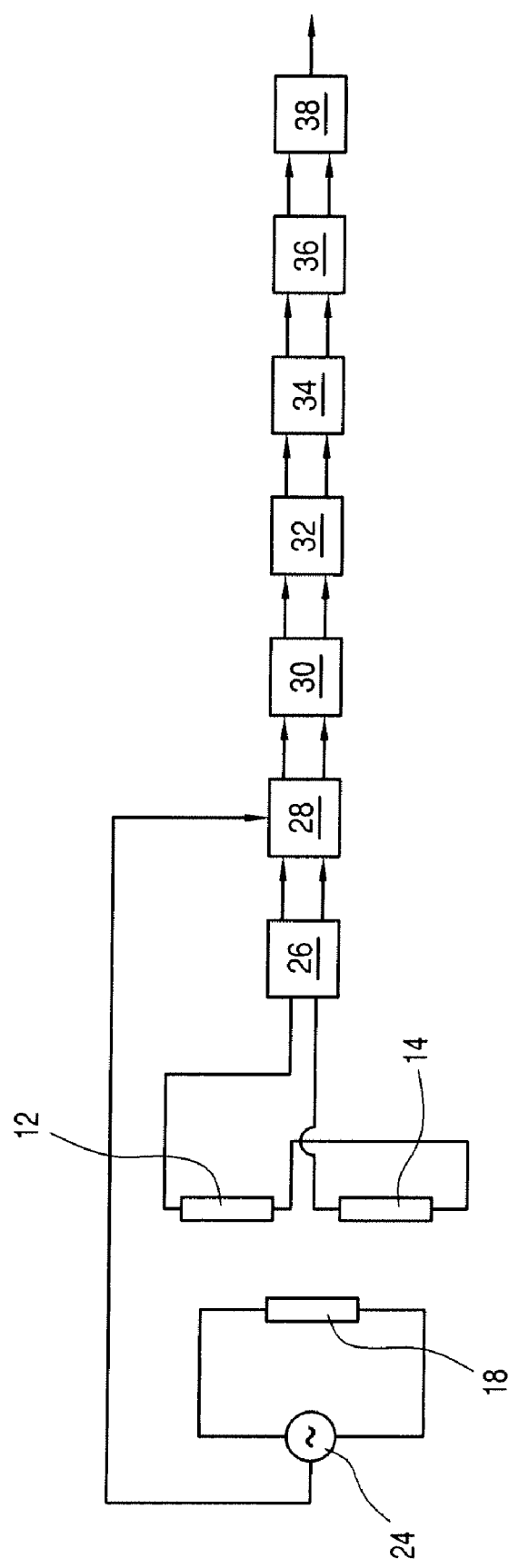
FIG. 2 is a block diagram of a device as shown in FIG. 1.

As shown in FIG. 2, the two receiver coils 12, 14 are connected subtractively as a difference coil, i.e., are arranged oppositely so that a voltage with the same absolute value but opposite sign is induced in coils 12, 14. Altogether, the transmitter coil 18 and the receiver coils 12, 14 form a transformer arrangement, the transmitter coil 18 forming the primary side and the receiver coils 12, 14 forming the secondary side. The transformer core in this arrangement is formed by the materials or media penetrating the coils 12, 14, 18, i.e., air, the housing 22, the pipe 10, and the liquid 16 with particles 20.

The impedance difference of the coils 12, 14 which is caused by the particles 20, i.e., the difference of the impedance of the two coils 12, 14 caused by the instantaneous presence of a particle 20 in one of the two coils 12, 14 (the particles 20 are much smaller than the distance of the coils 12, 14), is formed by the measurement signal which has been output from the coils 12, 14.

An oscillator 24 supplies the transmitter coil 18 with a suitable alternating current voltage which is preferably in the range between 20 kHz and 500 kHz in order to produce a measurement signal in the receiver coils 12, 14 via the eddy currents induced by the electrically conductive particles 20. The measurement signal delivered to the coils 12, 14 is supplied via an input stage 26 with a preamplifier to a unit 28 in which demodulation with respect to the transmitter frequency of the oscillator 24 takes place, and either an absolute value can be formed, or alternatively, two-channel demodulation takes place with a phase shift of 90° between the two channels. In the latter case, the subsequent signal path is then made two-channel. This version is shown in FIG. 2. The demodulated signal is then routed through a filter 30 which, by means of a lowpass filter, filters out the carrier frequency, and by means of a highpass filter, filters out the coil offset voltage (fundamentally, in a difference coil as a result of difference formation (the individual coils of the difference coil are not exactly the same in practice), a so-called coil offset voltage is formed which can exceed the actual difference signal, for example, by two to three orders of magnitude). The signal which has been filtered, in this way, is then amplified by means of an amplifier 32 and routed through a preferably variable bandpass filter 34 which optionally filters out the noise superimposed on the signal.

The signal which has been filtered by the bandpass filter passes through a phase controller 36 which makes it possible to adjust the phase angle of the signal in a manner favorable to evaluation before the signal is fed into an evaluation unit 38 which determines the amplitude and the phase angle of the measurement signal originating from the particles 20 in the conventional manner. This signal can be displayed, for example, in an orbital representation on a screen. Advantageously, the evaluation unit 38 is made such that counting of the detected particle passages takes place in order to be able to draw a conclusion about the particle concentration in the liquid 16, and thus, optionally, the machine state.

Instead of using the "normal difference coil" as shown in FIGS. 1 & 2 which comprises two subtractively connected coils, a multi-difference coil could also be used which, then, for example, has four receiver coils, each of the two receiver coils 12, 14 of the normal difference coil being replaced by two receiver coils connected back to back. A multi-difference coil has better noise suppression, i.e., a better signal-to-noise ratio than a normal difference coil, and the signal form is more pronounced. In any case, the structure is more complex and the signal amplitudes are smaller. Possibly disruptive pre- and post-oscillations are also obtained.

The signal generated by the difference coil when a particle passes through will be called the "difference signal" below.

The size of the detected particles is, for example, between 1 and 25 μm. Larger particles are conventionally filtered out of the lubricant to prevent damage to the machine.

Advantageously, the number of detected particles per unit of time is determined, from which the concentration of electrically conductive particles in the liquid can be determined since the liquid flow rate is usually known and is essentially constant.

Not only can passage of a particle be detected from the evaluation of the difference signal of the receiver coils, but also additional information can be obtained, especially with respect to the radial position of the particle as it passes through the receiver coils, i.e., the radial distance of the particle from the wall of the receiver coils, the flow velocity of the detected particle, the size of the detected particle and of the volumetric flow, i.e., the flow velocity of the liquid 16 averaged over the cross section of the pipe section 10. How such additional information can be obtained will be explained below using FIGS. 3 to 6 by way of example.

Generally, for a particle counter, it is also desired to detect the volumetric flow in order to be able to normalize the counted particles to a volume (particle/ml) and to assign them to existing standard tables. In this connection, at a given pipe diameter, the velocity of the liquid must be measured, from which then the volume of the lubricant which has passed the particle counter during the measurement time (typically 1 to 30 minutes) can be computed. While there are fundamentally many different—more or less complex—approaches, based on temperature measurement, ultrasound, pulses from mechanical mill wheels, etc., it is especially advantageous to derive the volumetric flow from the eddy current signals which are detected anyway for particle counting. In this way, a design without additional sensors can be implemented; this leads to lower costs, lower failure probability and a smaller space requirement. In this case, the flow velocity can only be detected when particles are recognized. However, generally, this is not a problem, since the measurement only takes place anyway when particles are also recognized.

Furthermore, it is advantageous for a particle counter to estimate the size of the detected particles and to classify the detected particles according to the estimated size in order to achieve a characterization of the machine state as definitive as possible. For example, when a given boundary value for the number of particles which have been detected overall or a given boundary value for the number of particles of a certain size class per unit of time is exceeded, an alarm signal can be output.

Since both the amplitude and also the time behavior of the difference signal caused by a particle depend on the radial position of the particle in the pipe section 10 or in the coil, it is advantageous both for velocity measurement and volumetric flow measurement as well as for particle size measurement to estimate the radial position of the particle and to correct the velocity measurement or size measurement accordingly.

Figure 3:
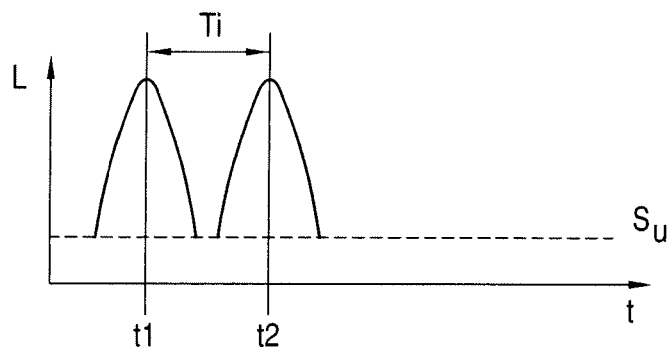
FIG. 3 shows the idealized behavior of the absolute value of the signal of the receiver coils from FIG. 1, the measured values having been cut off below a threshold value.
Figure 4:
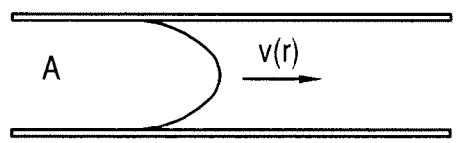
FIG. 4 shows a schematic of the theoretical radial velocity distribution in a laminar flow in a pipe.

FIG. 3 shows an example of the idealized behavior of the absolute value of the difference signal of a normal difference coil, such as, for example, the difference coil formed from the receiver coils 12, 14 from FIG. 1, the measured values having been cut off below the amplitude threshold value $S_u$ (the signal which has been cut off comprises base noise and the start and end of the difference signal). As long as the signal amplitude is above the threshold value $S_u$, the signal is recorded and stored in the processor of the evaluation unit. Two separate signal arcs are obtained which each have a peak at time $t_1$ and $t_2$. The respective amplitude peak, i.e., the respective instant $t_1$ and $t_2$, can be determined, for example, by a parabolic balancing computation or more simply by a maximum value search. For subsequent evaluation, what is decisive is the value of the amplitude peak $A_i$ and the time difference $T_i$ which follows from the difference between $t_1$ and $t_2$. For each counter event, i.e., for each found particle i, the corresponding maximum amplitude $A_i$ of the difference signal (optionally, also complex) and the pertinent time difference $T_i$ are stored.

Since the two difference coils 12, 14 have a spacing $d_{Sp}$ in the axial direction, the time difference $T_i$ in a first approximation is proportional to the flow velocity $v_i$ of the particle. The axial distance of the coils is reflected in the so-called effective width WB of the difference coil. Fundamentally, the relationship $v_i = k \cdot WB/T_i$ applies. The factor k depends on certain properties of the difference coil and can be determined at the factory one time for the respective type of particle counter.

Figure 5:
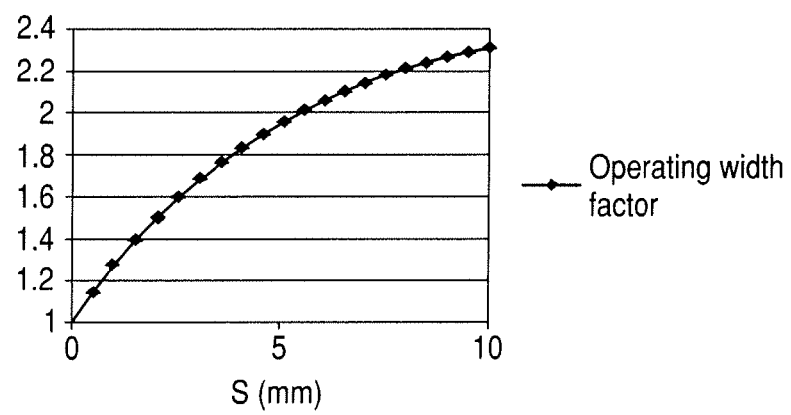
FIG. 5 is graph showing an example of the relationship between the effective width of the receiver coils from FIG. 1 and the radial position of a detected particle.

The effective width WB depends on the radial position of the particle upon passage through the difference coil, and increases with an increasing radial distance of the particle from the coil wall. This fact can be taken into account by the dependency of the effective width on the radial position of the particle being empirically determined at the factory for the respective type of particle counter. FIG. 5 shows one example for the relative increase of effective width with increasing radial particle distance s. Using this empirical curve, as is described more fully below, the measured time difference $T_i$ can be corrected with respect to the radial distance of the particle i.

Figure 6:
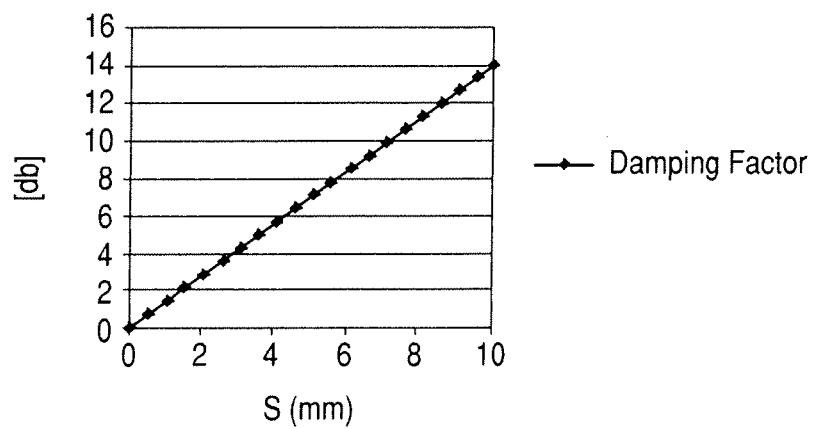
FIG. 6 is a graph showing an example of the relationship between the attenuation of the signals of the receiver coils from FIG. 1 and the radial position of a detected particle.

Fundamentally, the maximum amplitude $A_i$ of the difference signal is a measure of the size of the particle i. However, in this connection, it must be considered that the attenuation of the difference coil depends on the radial position s of the particle so that, for a reliable estimation of the particle size, the measured maximum amplitude $A_i$ must be corrected accordingly. This can take place by the dependency of the attenuation of the difference signal on the radial distance s from the coil wall being empirically determined at the factory for the respective type of particle counter. FIG. 6 shows an example of such a correction curve. The farther the particle is radially from the coil system, the weaker the signal amplitude becomes. Here, the size of the particle also plays a certain part; the attenuation function with respect to distance, however, will run essentially the same.

Furthermore, with respect to the particle velocities, it must still be considered that the velocity of a laminar flow in a pipe depends, in the known manner, on the radial distance r from the pipe wall, the dependency being parabolic and the maximum flow velocity being in the center of the pipe. Therefore, a certain distribution of the particle velocities, and thus, of the measured time differences $T_i$ is obtained for this reason.

In the evaluation of the difference signals, it is a good idea to make the following assumptions.

1. During a measurement interval of typically 1 to 30 minutes, the volumetric flow remains essentially constant. This, of course, also depends on the respective system. In practice, velocity fluctuations occur essentially when the system is started. During this time, however, no particle measurement takes place anyway. Otherwise, changes of the volumetric flow arise mainly due to fluctuations of the ambient temperature (effect on the viscosity of the lubricant) and due to the slowly changing permeability of the lubricant filter. Only in case of faults can rapid changes of the flow velocity occur, for example, if a filter breaks.

2. The radial distance s of the particles to the coil system is uniformly distributed when viewed statistically.

3. Turbulent flow does not occur. This can be ensured by guide elements.

4. All particles are much smaller in their extension than the effective width of the coils.

One example for evaluation of the difference signals is described below.

As already mentioned, during a measurement interval of typically 1 to 30 minutes, the maximum amplitude $A_i$ and the time difference $T_i$ for each detected particle i are stored. In order to enable reliable evaluation, a certain minimum number of particles should be determined. Optionally, for a small particle concentration, the measurement interval must be lengthened accordingly. As a result, a certain distribution of the maximum amplitudes and the time differences is obtained. The smallest time differences $T_i$ represent particles in the center of the coil arrangement, i.e., $s = r_0$. For the distribution of the flow velocity v(r) of a laminar flow in a pipe, the following applies:

$$v(r) = \frac{\Delta p}{4 \cdot l \cdot \eta} \cdot (r_0^2 - r^2)$$

Here, $\Delta p$ is the pressure difference in pascals, l is the length of the pipe in meters and $\eta$ is the kinematic viscosity in Pa s.

The actual maximum velocity in the pipe can be estimated by the smallest measured time difference $T_i$ being divided by the "effective width" factor FW for $r_0$:

$$T' = \text{Min}(T_i)/FW(r_0).$$

Since we know the actual geometrical coil distance $d_{Sp}$ and now also the corrected time T', the maximum speed $v_{max}$ can be computed:

$$v_{max} = d_{Sp}/T'.$$

For the mean velocity this yields $v_{mean} = v_{max}/2$. The following applies to the volumetric flow:

$$I = v_{mean} r_0^2 \pi.$$

Since $v_{max}$ is known at this point, the constant $\Delta p/l\eta$ can be determined:

$$c = \frac{\Delta p}{l \cdot \eta} = \frac{4 \cdot v_{max}}{r_0^2} \qquad 5$$

Thus, the actual velocity distribution v(r) and v(s) in the pipe is now known. Therefore, the corrected time differences $T'_i(s)$ can be determined according to a computed effective width:

$$T'(s) = \frac{d_{Sp}}{v(s) \cdot FW(s)} = \frac{d_{Sp}}{\frac{c}{4}(r_o^2 - (r_o - s)^2) \cdot FW(s)} \qquad 15$$

Thus, for example, a table with values $T'_i(s)$, as a function of the radial distance s of the particle i to the coil, is obtained. In the simplest case, this table can be used as a look-up table in order to assign a radial distance to the coil s for each particle i found. In this connection, the measured value $T_i$ is taken and the nearest value $T'_i(s)$ is sought in the table.

By means of this distance assignment, not only can the measured time difference, and thus, the computed particle velocity be corrected, but the measured maximum amplitude $A_i$ can also be corrected using the dependency of the difference signal attenuation on the radial particle distance s which has been empirically determined beforehand. In this case, the amplitude value in the simplest case is reduced to a scalar, advantageously, to the maximum value of the representation of the absolute value of the difference signal from FIG. 3. This value is then corrected with the respective attenuation value. Then, the value can be evaluated using the evaluation thresholds (for example, eight evaluation thresholds). Each evaluation range corresponds to a range of particle sizes. For each range, there is a counter which is incremented when the measured particle amplitude falls in this range. After the measurement interval, the total volume of the liquid is computed using the measurement duration and the determined volumetric flow and a contamination class is demonstrated according to the counts, for example, according to ISO 4406. Alternatively, the amplitude evaluation can take place based on a vector which has been assigned to the respective particle using the difference signal (in this connection, not only the maximum amplitude value, but also the phase are considered).

It goes without saying that the empirically determined correction functions as shown in FIGS. 5 and 6 can be represented by means of a balancing computation by suitable functions, for example, approximated parabolas and their inverse function. In this case the look-up table can be omitted.

Immediately after turning on the particle counter, the flow velocity is still unknown, and thus, under certain circumstances, the particles cannot be reliably distinguished, since the assignment of the individual absolute-value signal arcs to the difference signal without knowledge of the expected range of the time differences $T_i$ to a certain event, specifically the passage of a particle, is not always reliably possible. To circumvent this problem, as a "starting aid," after exceeding the lower threshold value $S_u$ a signal can be recorded of a length which is sufficient for recognizing a minimum flow velocity. The detected difference signals can then be separated using such a detected typical behavior or assigned to individual particle passages. This separation can take place, for example, by means of cross correlation with variation of the given effective widths or time differences $T_i$. In this connection, the given effective width or the given time difference is varied such that the amplitudes of the cross correlation function are maximized.

What is claimed is:

1. Process for detecting electrically conductive particles in an electrically nonconductive liquid flowing in a pipe section, comprising the steps of:
   inducing eddy currents in the particles in the flow of electrically nonconductive liquid by means of a transmitter coil surrounding the pipe section,
   outputting a difference signal according to the eddy currents induced by the transmitter coil by means of at least one first inductive receiver coil surrounding the pipe section and a second inductive receiver coil which is spaced axially relative to the first receiver coil and which surrounds the pipe section, the receiver coils being located in a region of the transmitter coil and being subtractively connected in a manner causing the transmitter coil to form a primary side and the receiver coils to form a secondary side of a transformer arrangement, and
   evaluating the difference signal to detect passage of electrically conductive particles in the pipe section and the position of detected particles within the pipe section,
   using the evaluation of the difference signal to determine particle concentration in the liquid, and
   determining the state of a machine though which the liquid has passed from said particle concentration,
   wherein a radial distance of the detected particles from a wall of the receiver coils is estimated from the difference signal, and
   wherein a flow velocity of the detected particles flowing in the pipe section is estimated from the difference signal.

2. Process in accordance with claim 1, wherein the pipe section is part of a lubricant circuit.

3. Process in accordance with claim 2, wherein the liquid is lubricating oil of a machine.

4. Process in accordance with claim 1, wherein the transmission frequency of the transmitter coil is between 20 kHz and 500 kHz.

5. Process in accordance with claim 1, wherein the size of the detected particles is between 1 and 25 μm.

6. Process in accordance with claim 1, wherein the number of detected particles per unit of time is determined.

7. Process in accordance with claim 1, comprising the further step of outputting an alarm signal when a predetermined boundary value for the number of detected particles per unit of time is exceeded.

8. Process in accordance with claim 1, wherein only difference signals that have an amplitude which exceeds a certain threshold are used for particle detection.

9. Process in accordance with claim 8, wherein the difference signal is recorded for as long as the signal amplitude exceeds the threshold value.

10. Process in accordance with claim 1, wherein the flow velocity of the detected particles is estimated from a time interval of peak and minimum values of the difference signal.

11. Process in accordance with claim 10, wherein the flow velocity of the detected particles is estimated from the time interval of the peaks of the absolute value of the difference signal.

12. Process in accordance with claim 10, wherein a distribution of the determined time intervals is determined and subjected to statistical analysis.

13. Process in accordance with claim 12, wherein a theoretical radial distribution of the flow velocity in a laminar flow is considered in the statistical analysis of determined time intervals.

14. Process in accordance with claim 13, wherein the flow velocity of the liquid is determined from a peak value of the estimated particle velocities with consideration of a geometrical distance of the receiver coils.

15. Process in accordance with claim 1, wherein the estimated radial distance of the detected particles from the receiver coil wall is used in the estimation of the flow velocity of the particles.

16. Process in accordance with claim 15, wherein the relationship between an effective width of the receiver coils with respect to the radial distance of the detected particle from the receiver coil wall is empirically determined beforehand.

17. Process in accordance with claim 16, wherein a theoretical radial distribution of the flow velocity in a laminar flow, a geometrical distance of the receiver coils and the relationship of the effective width of the receiver coils with respect to the radial distance of the particles determined beforehand are considered in the estimation of the radial distance of the detected particles from the receiver coil wall.

18. Process in accordance with claim 1, wherein the size of the detected particles is estimated from the difference signal and the detected particles are classified according to the estimated size.

19. Process in accordance with claim 18, wherein a radial distance of the detected particles from a wall of the receiver coils is estimated from the difference signal, and wherein the estimated radial distance of each detected particle from the wall of the receiver coils is used in the estimation of the particle size.

20. Process in accordance with claim 19, wherein the relationship of the amplitude of the difference signal with respect to the radial distance of the particle from the receiver coil wall is empirically determined beforehand.

21. Process in accordance with claim 20, wherein a theoretical radial distribution of the flow velocity in a laminar flow, a geometrical distance of the receiver coils, the dependency of the effective width of the receiver coils on a radial distance of the particles from the receiver coil wall determined beforehand, and the relationship of the amplitude of the difference signal with respect to the radial distance of the particles from the receiver coil wall determined beforehand are considered in the estimation of size of the detected particles.

* * * * *